United States Patent [19]

Theeuwes

[11] 4,203,440
[45] May 20, 1980

[54] DEVICE HAVING VARIABLE VOLUME CHAMBER FOR DISPENSING USEFUL AGENT

[75] Inventor: Felix Theeuwes, Los Altos, Calif.

[73] Assignee: Alza Corporation, Palo Alto, Calif.

[21] Appl. No.: 953,489

[22] Filed: Oct. 23, 1978

[51] Int. Cl.² ............................................. A61M 31/00
[52] U.S. Cl. ..................................... 128/260; 222/386.5
[58] Field of Search ................... 128/213 R, 232, 260, 128/261-262, 271; 424/14, 25, 27; 222/386.5

[56] References Cited

U.S. PATENT DOCUMENTS

| | | | |
|---|---|---|---|
| 3,760,984 | 9/1973 | Theeuwes | 128/260 |
| 3,865,108 | 2/1975 | Hartop | 128/260 |
| 3,971,376 | 7/1976 | Wichterle | 128/260 |
| 3,987,760 | 10/1976 | Eckenhoff et al. | 128/260 |
| 3,995,631 | 12/1976 | Higuchi | 128/260 |

*Primary Examiner*—Robert W. Michell
*Assistant Examiner*—C. F. Rosenbaum

*Attorney, Agent, or Firm*—Paul L. Sabatine; Thomas E. Ciotti; Edward L. Mandell

[57] ABSTRACT

A self-powered device is disclosed for delivering a useful agent. The device comprises (1) a housing member, (2) a variable volume chamber storing a useful agent and having a passageway for delivering the agent in the housing, and (3) a pressure generating member comprising a semipermeable polymer having a cross-linked hydrophilic polymer dispersed therein positioned between the housing and the chamber. In operation, when the device is in a fluid environment, fluid from the environment enters the housing and is imbibed by the hydrophilic polymer into the generator, causing the generator to enlarge and apply pressure against the chamber, thereby decreasing the volume of the chamber and simultaneously dispensing agent through the passageway from the device at a controlled rate over a prolonged period of time. An article of manufacture also is disclosed which consists of a pressure generating member manufactured as a film useful for making a dispensing device.

17 Claims, 6 Drawing Figures

U.S. Patent
May 20, 1980
4,203,440
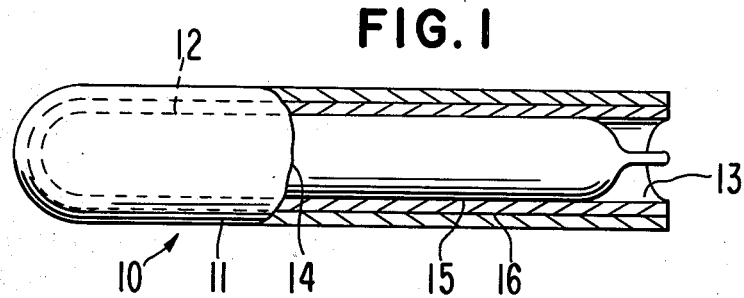
FIG. 1
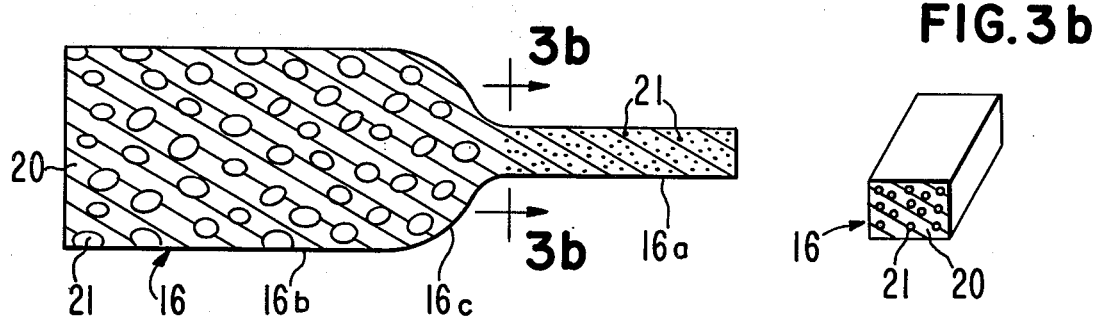
FIG. 2a    FIG. 2b
FIG. 3a    FIG. 3b
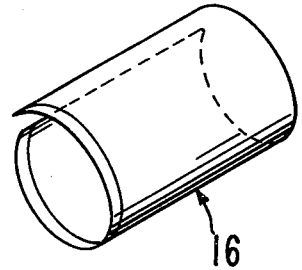
FIG. 4

DEVICE HAVING VARIABLE VOLUME CHAMBER FOR DISPENSING USEFUL AGENT

FIELD OF THE INVENTION

This invention pertains to a self-powered, integrated unit device for delivering a useful agent. More particularly, the invention relates to a device that is simple in construction, and delivers an agent in response to a hydrostatic force exerted by an expanding resinpolymer composition on a chamber containing agent. The force causes the chamber to continuously collapse and decrease its internal volume, thereby delivering agent from the device.

BACKGROUND OF THE INVENTION

In recent times much effort has been devoted to developing new and useful osmotic powered devices for delivering useful agents to a predetermined environment of use. For example, U.S. Pat. No. 3,760,984 issued to Theeuwes discloses a device comprising an inner collapsible container carrying on its outer surface a layer of an osmotic solute and a distinct layer of a polymer permeable to fluid and impermeable to the solute. The device has an inventive means for filling the container. In U.S. Pat. No. 3,971,376 issued to Wichterle, a device is disclosed comprising a capsule having a unitary wall formed of a substantially non-collapsible elastic material that is exposed to the environment of use. A textile fabric is embedded in the elastic material to impart strength and minimize problems due to the inherent mechanical properties of the material that occur during uptake of fluid. In U.S. Pat. No. 3,995,631 issued to Higuchi, et al., there is disclosed a bag formed of a flexible material encapsulated with a film of an osmotically effective solute surrounded by a wall having in at least a part controlled permeability to an exterior fluid. The above described osmotic devices are useful for delivering many agents, and they represent a valuable contribution to the agent delivery art. The present invention is an advancement in the osmotic delivery art by making available a new pressure generating means that can supply the self-contained power needed for propelling an agent from an osmotic device.

OBJECTS OF THE INVENTION

It is an immediate object of this invention to make available a new and useful osmotic delivery device that is self-contained and self-powered and represents an improvement in the delivery art.

Another object of the invention is to provide an osmotic device that is simple in construction, and which device can produce the practical benefits of controlled and continuous administration of drugs to animals including humans over a prolonged period of time.

Yet another object of this invention is to provide an improved device having a variable volume chamber which enables from low to high concentrations of active agent to be administered from the device, and which concentrations of agent will not be leached from the device, nor have their potency decreased during delivery to the environment of use.

Still another object of the present invention is to provide a delivery device that is easy to manufacture and will deliver thixotropic formulations, at a controlled rate over a prolonged period of time.

Other objects, features and advantages of this invention will become more apparent from the following detailed description when taken in conjunction with the accompanying specification, drawings, and the claims.

SUMMARY OF THE INVENTION

This invention concerns a device for delivering a beneficial agent to an environment of use. The device comprises a pressure generating member surrounding a variable volume chamber filled with agent and positioned in a rigid housing member. In operation, the device releases agent in response to the pressure generator imbibing fluid, enlarging and expanding, thereby internally pressurizing the device and exerting pressure on the chamber which diminishes in volume and urges agent from the device.

BRIEF DESCRIPTION OF THE DRAWINGS

In the drawings, which are not drawn to scale, but are set forth to illustrate various embodiments of the invention, the figures are as follows:

FIG. 1 is a side view, partly in opened-section, of an osmotic dispensing device made according to the invention;

FIGS. 2a and 2b are full opened-section views of the device of FIG. 1, depicting both the structure and the operation of the device;

FIGS. 3a and 3b are illustrations of the integral, unit pressure-generating member provided by the invention; and, FIG. 4 illustrates one of the structural embodiments of the pressure-generating member provided for easy manufacturing of the osmotic device.

In the drawings and specification, like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Turning now to the drawings in detail, which are an example of a new and useful device for dispensing an agent, and which example is not to be construed as limiting, one device is indicated in FIG. 1 by numeral 10. In FIG. 1, device 10 consists essentially of a housing 11 designed, shaped, sized and adapted for placement and retention in the environment of use. Housing 11, in a presently preferred embodiment is made of a substantially rigid wall forming material, which surrounds and defines an internal space for receiving a variable volume chamber 12. Housing 11 has at least one opening 13, or it can have more than one opening through which chamber 12 communicates with the exterior of device 10 and exterior fluid is admitted with device 10. Chamber 12 is seen in dashed lines in FIG. 1, and its outer surface 15 is seen at the opened-section 14 of housing 11. Chamber 12 is formed of a flexible material that can collapse in response to pressure applied against exterior surface 15. The movement of chamber 12 from a resting state to a collapsed state produces an internal variable volume change, as seen in FIGS. 2a and 2b, that propels agent from device 10.

Referring to FIGS. 2a and 2b, dispensing device 10 of FIG. 1 is seen in opened-section comprising housing 11 formed of a substantially shaped retaining rigid material having positioned therein pressure-generating member 16 and variable volume chamber 12. Chamber 12 is partially or completely surrounded by member 16.

Member 16 is positioned adjacent to the interior surface of housing 11 and exterior surface 15 of chamber 12. Member 16 is formed of a semipermeable material containing a lightly cross-linked hydrophilic, swellable polymer, which polymer in one embodiment is in the form of a multiplicity of ion-exchange beads 21, seen in FIGS. 3a and 3b. Chamber 12 is formed of an elastomeric, or other low modulus material, and it, 12, has a passageway 18 for dispensing agent 17 from device 10 to the environment of use. Passageway 18, in one embodiment, is formed by the wall of chamber 12 terminating in passageway 18, which is projected through opening 13 of housing 11. In another embodiment, not shown, passageway 17 is an aperture in the wall of chamber 12 and it is connected to a conduit or tube that extends through opening 13 for releasing agent 17 from device 10.

In operation, member 16 imbibs external fluid into housing 11 through opening 13, or in another embodiment fluid can enter through an additional opening positioned in housing 11. Member 16, in the presence of imbibed fluid increases its space-occupying dimensions from 16a to 16b, thereby pressurizing device 10. The internal pressure generated by member 16 is applied against exterior surface 15 of chamber 12, causing chamber 12 to slowly collapse from position 19a to 19b. The collapse of chamber 12 correspondingly decreases the internal volume, a reservoir, of chamber 12 thereby expelling agent 17 at a predetermined and controlled rate through passageway 18 to the environment of use over a prolonged period of time. The rate of imbibition of member 16 coupled with the rate of change of chamber 12 correspondingly act to control the rate of release from device 10. The size of passageway 18 can, in an optional embodiment, be given predetermined dimensions as an additional aid for controlling the rate of agent 17 released by device 10.

FIGS. 3a and 3b illustrate in opened-section the structure of pressure generating member 16. Member 16 consists essentially of semipermeable polymer film 20 containing a cross-linked hydrophilic polymer, which in the presently preferred embodiment consist of a plurality of ion-exchange beads or droplets 21 dispersed therein. In operation, as fluid is imbibed into member 16, it swells from rested state 16a, by swelling and expanding, as seen in 16b. FIG. 3b depicts the change occuring at 3b—3b interface as fluid is absorbed by beads 21. The swelling front 16c continuously moves as fluid is imbibed into member 16 in the direction of the arrow from 16b through 16c to 16d. This imbibition activity produces an internal hydrostatic pressure that is applied against chamber 12. The rate of volume swelling of member 16, expressed as dv/dt is proportional to: the area exposed to fluid of member 16, the permeability of the semipermeable polymer 20 forming member 16, the imbibition pressure of beads 21, the weight of resin beads 21 in member 16, and inversely proportioned to the weight of semipermeable polymer 20 in member 16, and the particle diameter of the dispersed beads.

FIG. 4 illustrates member 16 in one shaped embodiment that can be useful for manufacturing device 10. Member 16, in the shown embodiment, is fabricated as a rate controlling, rolled film or rolled strip. The strip is inserted around flexible chamber 12, perforated in one design, in constant volume housing 11. The strip functions as described above, that is, it imbibes fluid, swells, emlarges, and generates an internal pressure that is applied against chamber 12 urging it to collapse and dispense agent 17 through passageway 18 from device 10.

DETAILED DESCRIPTION OF THE INVENTION

Device 10, as used for the purpose of this invention consists of housing 11 made of a polymer possessing rigid properties. This material permits pressure to be exerted against it without any major change in its shape or dimensions, thereby assuring that pressure generated in device 10 is exerted against chamber 12. Housing 11 can be formed of a member selected from the group consisting of a fluid impermeable material having at least one opening for letting fluid into device 10, from a fluid permeable material, or a microporous material having a path for the passage of fluid. Representative polymers suitable for forming housing 11 include polyolefins such as polyethylene, polypropylene, and polytetrafluoroethylene, polyamide, polyformaldehyde, polystyrene, polycarbonate, polyacetal, polyarylate, polymethacrylate, polyacrylonitrile, rigid polyvinyl chloride, polyamide, ebonite, the copolymeric derivatives of the polymers, and the like. Generally, the thickness of housing 11 will vary depending on device 10 and its use, and it will usually have a thickness of 0.25 mm to 15 mm, or more.

Representative materials suitable for manufacturing chamber 12 are materials that can be designed into a shaped, variable volume chamber, including an elastomeric flexible type of capsule, which collapses in response to applied pressure, thereby dispensing agent. Typical flexible, elastomeric polymers include natural rubber, often identified by the synonyms poly(2-methyl-1,3-butadiene) and cis-1,4-polyisoprene, gutta percha or trans-polyisoprene, cyclised rubber, synthetic isoprene rubber, butadiene rubber, styrene-butadiene rubbers, nitrile rubber, chloroprene rubber, ethylene-propylene rubbers, butyl rubbers, and the like as disclosed in *Handbook of Common Polymers*, by Scott and Roff, Sections 29 through 40, 1971, published by the Chemical Rubber Company, Cleveland, Ohio. Chamber 12, formed of the representative materials, can have its wall of varying thickness, usually about 0.25 mm to 15 mm, or more, depending on the chamber and its uses. Chamber 12 can be manufactured with one or more passageways for dispensing agent, or it can be made to form a passageway when the device is in the environment of use. In this latter embodiment, one end of chamber 12 is closed with a water-soluble plug of an erodible material, such as polyvinyl alcohol, gelatin, or the like, that erodes in the environment of use to form a small-diameter orifice. In another embodiment, a preferred orifice having a cross-section of 1 to 10 mils can be temporarily closed with a plug, which plug is ejected when the chamber starts to collapse and pump agent during use, thereby forming the orifice in situ.

Representative of materials suitable for forming pressure-generating member 16 include semipermeable polymers 20 that are permeable to the passage of fluid, substantially impervious to the passage of the swellable, insoluble hydrophilic polymer manufactured in the form of ion-exchange particles 21 and they 20 are inert. The semipermeable polymers include a member selected from the group consisting of cellulose esters, cellulose ethers, cellulose mixed esters and ethers, cellulose acrylate, cellulose diacylate, cellulose triacylate, cellulose acetate, cellulose diacetate, cellulose triacetate, polyurethane, polyesters, polyamides, and the like.

In a presently preferred operative embodiment semipermeable polymer 20 contains a plasticizer that imparts flexibility and stretchability to polymer 20. Representative plasticizers suitable for the present intent include phthalates, phosphates, citrates, succinates, glycolates, glycols, diols, polyols, and the like. The semipermeable polymers are disclosed in U.S. Pat. No. 4,058,122. The hydrophilic, insoluble polymers 21 that can be homogeneously or heterogeneously dispersed in the semipermeable polymer 20 include ion exchange polymers. The latter polymers include anion and cation resins that are particle, bead and droplet shaped. The particle size can vary and it usually is of 10 to 350 mesh. The resins can be homopolymers, copolymers, derivatives thereof, and cross-linked resins. Typical resins include ion exchange resins such as polystyrene, cross-linked styrene-divinylbenzene, cross-linked acidic cation resins, cross-linked basic anion resins, anion resins—$C_6H_4$—$CH_2N(CH_3)_3Cl$ which is a strongly basic resin with quaternary ammonium groups attached to a styrene divinylbenzene copolymer lattice, anion resin—$C_6H_4$—$CH_2N(CH_3)_3(C_2H_4OH)Cl$ a quaternary group on the styrene divinylbenzene lattice, anion resin—$C_6H_4CH_2N(CH_3)_3Cl$ attached to styrene divinylbenzene lattice with a surface area of approximately 23 meters $^2$/dry gram of resin, cation resin—$C_6H_4$—$SO_3H$ composed of nuclear sulfonic groups attached to a styrene divinylbenzene polymeric lattice, weak acid cation resin—$C_6H_4$—$CH_2N$—$(CH_3)_3OOCH_2C$-R, where R is alkyl, made by polymerizing acrylic acid inside quaternary styrene divinylbenzene copolymer lattice to produce spherical resin beads containing paried anion and cation sites, bead-formed cross-lined dextran gel substituted with a group selected from diethylaminoethyl, diethyl—(2-hydroxypropyl)-aminoethyl, carboxymethyl and sulphoprophyl, sulfonated phenolic ion resins, cross-linked acrylic and phenol-formaldehyde resins, and the like.

As specific examples of these ion-exchange resins 21 mentioned can be made of strongly acidic ion-exchange resins such as Amberlite ® IR-120 (Rohm & Haas Company), Diaion ® SK-1 (Mitsubishi Chemical Co.), Dowex ® 50W (Dow Chemical Company), Duolite ® C-20 (Diamond Alkali Co.), the strongly basic ion-exchange resin such as Amberlite ® IRA-400, Diaion ® SA-10A, Dowex ® 1,2, Duolite ® A-101, the weakly basic ion exchange resins such as Amberlite ® IR-45, Duolite ® A-2, A-41 contains quaternary ammonium and tertiary amine groups, Dowex ® 4, the Sephadex ® resins, and the like. The resins are known in U.S. Pat. No. 3,689,632 and in *Diffusion and Membrane Technology,* ACS Monograph, No. 156, Chapter 11, 1962.

The resin beads 21 can be dispersed in a semipermeable polymeric film by methods known to the manufacturing art. For example, to 80% by weight of semipermeable cellulose acetate having an acetyl tent of 32% and plasticized with polyethylene glycol having a molecular weight of 400 in a methylene chloride-methanol solvent, 80:20 weight: weight, is added 20% by weight lightly cross-linked polyacrylamide beads with stirring to disperse the beads therein. A thin film is formed by air spraying on a casting surface followed by drying in a vacuum oven. The water retention capacity, WRC, or percent water imbibed and retained, can be regulated by varying, in one embodiment, the cross-linkage and the resin form. The water retention capacity increases with decreasing cross-linkage, as it is able to imbibe more water compared to higher cross-linked resins. The degree of permeability, DP, or the passage to water, of a semipermeable polymer, can in one embodiment, be governed by selecting the degree of substitution, for example, the degree of acylation of the semipermeable cellulosic polymer. The present invention provides a means for regulating the rate of imbibition, RI, of pressure generating member 16 by governing in combination the degree of cross-linkage, DC, and the degree of substitution, DS. The semipermeable film forming member 16 can be from 1 mm to 15 mm thick, and it houses from 1 to 40% by weight of ion-exchange particles per total weight of film.

The term active agent as used herein means any compound that can be delivered to produce a useful, or a beneficial result. The term includes algicide, antioxidant, biocide, germicide, fungicide, pesticide, rodenticide, insecticide, plant growth promoter, plant growth inhibitor, preservating agent, surfactant, disinfectant, catalyst, sterilization agent, chemical reactant, fermentation agent, cosmetic, food, nutrient, food supplement, drug, vitamin, sex sterilant, fertility inhibitor, fertility promoter, air purifier, microorganism attenuators, antiallergenic, and other compounds that benefit the surroundings, the environment, and the habitat.

Exemplary drugs that can be administered according to the spirit of the invention include locally and systemically acting drugs. These drugs include a member selected from the group consisting of physiologic and phamacologic acting drugs, such as gastrointestinal administerable drugs, central nervous and autonomic nervous system acting drugs, hypnotic, sedative, psychic energizer, tranquilizer, anticonvulsant, antiparkinson, muscle relaxant, analgesic, antipyretic, anti-inflammatory, anesthetic, antispasmodic, antimicrobial, antiviral, antiulcer, hormonal, sympathomimetic, diuretic, hypoglycemic, vitamin, contraceptive, and ophthalmic drugs. These beneficial drugs and their dose amounts for humans are known in *Drill's Pharmacology in Medicine,* edited by DiPalma, J. R., 1965, published by McGraw-Hill Book Company, New York, in *Pharmacological Basis of Therapeutics,* by Goodman and Gilman, 4th Edition, published by the McMillian Company, London; in *The Drug, The Nurse, The Patient,* edited by Falconer, Ezell, Patterson and Gustafson, 1974, published by W. B. Saunders Company, Philadelphia; and in U.S. Pat. No. 3,977,404, which patent is assigned to the ALZA Corporation of Palo Alto, California the assignee of this patent application. The drug in the chamber can be mixed with a pharmaceutically acceptable carrier, such as a liquid, water, saline, cottonseed oil, sesame oil, ethyl oleate, isopropyl myristate, propylene glycol, 0.01% gelatin in oil, and the like. The drug can be present in solution, in semi-solid, or paste formulation, in a thixotropic state and the like, which permits controlled dispensing of drug from device. Pharmaceutically acceptable carriers and the like are known to the art in *Remington's Pharmaceutical Sciences,* 14th Edition, pages 1461 to 1792, 1970, published by the Mack Publishing Company, Easton, Pennsylvania.

Representative examples of drugs that can be delivered from a device designed and adapted for oral administration comprises, (a) a housing manufactured from rigid polyethylene with an opening for admitting fluid, an opening for a passageway, and having housed therein, (b) a variable-volume chamber shaped and sized like a triple zero capsule with a single passageway for releasing drug and formed of flexible, natural rubber, which container is surrounded by a film interpositioned between the housing and the chamber, said film (c) a pressure generating film of semipermeable, plasticized cellulose acetate having an acetyl content of 32% with spherical particles of highly hydrophilic, lightly cross-linked polyacrylamide resin prepared by the copolymerication of acrylamide and N,N'-methylene-bis-acrylamide, and a drug formulation in the chamber, such as (d) the antibiotic tetracycline hydrochloride in pharmaceutically acceptable polyethylene glycol 200, or (e) micronized procaine penicillin in peanut oil with a small amount of aluminum monostearate, which embodiments are dispensed at a controlled rate for the device, when the device is in a fluid environment of use.

Although the foregoing invention has been described in detail by way of a full disclosure, illustrations of presently preferred embodiments, and examples for purpose of clarity of understanding, it will be understood that certain changes and modifications may be practiced within the scope and spirit of the invention.

I claim:

1. A device for delivering a useful agent to an environment of use, comprising:
   (a) a useful agent;
   (b) a housing having a shape retaining wall defining an internal space, the housing having at least one opening connecting the space with the exterior of the device;
   (c) a variable volume chamber in the housing, said chamber comprising a flexible wall surrounding a reservoir for storing the agent, and a passageway for delivering the agent from the chamber to the exterior of the device;
   (d) a pressure generating member in the housing positioned between the housing and the chamber, said member formed of a semipermeable polymer having therein a swellable, insoluble hydrophilic polymer; and,
   (e) wherein, in operation when the device is in the environment of use, the member imbibes fluid admitted into the device, causing the member to expand, generate and exert pressure on the chamber which decreases the volume of the chamber thereby delivering agent through the passageway from the device at a controlled rate over a prolonged period of time.

2. The device for delivering the useful agent to an environment of use according to claim 1, wherein the passageway of the variable volume chamber extends through the opening in the housing to the exterior of the device.

3. The device for delivering the useful agent to an environment of use according to claim 1, wherein the swellable hydrophilic polymer, is an ion exchange resin.

4. The device for delivering the useful agent to an environment of use according to claim 1, wherein the housing has an opening for the passageway and at least an additional opening for letting fluid into the housing.

5. The device for delivering the useful agent according to claim 1, wherein the housing is manufactured from a microporous polymer.

6. The device for delivering the useful agent to an environment of use according to claim 1, wherein the chamber is formed of a member selected from the group consisting of natural rubber, gutta percha, cyclised rubber, isoprene rubber, butadiene rubber, styrene-butadiene copolymeric rubber, nitrile rubber, chloroprene rubber and ethylenepropylene copolymeric rubber.

7. The device for delivering the useful agent to an environment of use according to claim 1, wherein the housing is formed of a member selected from the group consisting essentially of polyolefin, polyethylene, polypropylene, polytetrafluoroethylene, polyamide, polyformaldehyde, polystyrene, polycarbonate, polyacrylate, polymethacrylate, polyacrylonitrile, and polyvinyl chloride.

8. The device for delivering the useful agent to an environment of use according to claim 1, wherein the agent is a drug.

9. The device for delivering the useful agent according to claim 1, wherein the environment is a biological environment, and the agent is a drug selected from the group consisting of locally and systemically acting gastrointestinal, central nervous system, hypnotic, sedative, psychic energizer, tranquilizer, anticonvulsant, antiparkinson, muscle relaxant, analgesic, antipyretic, anti-inflammatory, anesthetic, antispasmodic, antimicrobial, antiviral, antiulcer, hormonal, sympathomimetic, diuretic, hypoglycemic and anticontraceptive drugs.

10. The device for delivering the useful agent according to claim 1, wherein the agent in the chamber is a drug mixed with a pharmaceutically acceptable carrier.

11. The device for delivering the useful agent according to claim 1, wherein the passageway is projected through the opening in the housing, with said passageway formed by the wall of the chamber.

12. The device for delivering the useful agent according to claim 1, wherein the passageway is connected to a tube that extends through the opening in the housing for delivering agent from the device.

13. The device for delivering the useful agent according to claim 1, wherein the pressure-generating member comprises a semipermeable polymer selected from the group consisting of a cellulose ester, cellulose ether, cellulose acylate, cellulose diacylate, cellulose triacylate, and polyurethane, having dispersed therein particles of a member selected from the group consisting of a cross-linked anion and cation resins.

14. The device for delivering the useful agent according to claim 1, wherein the swellable, insoluble hydrophilic polymer is an ion exchange resin selected from the group consisting essentially of cross-linked styrene-divinylbenzene copolymer, cross-linked basic acidic cation resin, cross-linked basic anion resin, anion resin—$C_6H_4$—$CH_2N(CH_3)_3Cl$, anion resin—$C_6H_4$—$CH_2N(CH_3)_3(C_2H_5$—$OH)Cl$, cation resin—$C_6H_4$—$SO_3H$, and acid cation resin—$C_6H_4$—$CH_2N(CH_2COOH)_2$.

15. The device for the delivery of the useful agent according to claim 1, wherein the swellable, insoluble hydrophilic polymer is present in the form of particles and the particles are bead and spherical shaped.

16. The device for delivery of the useful agent according to claim 13 wherein the semipermeable polymer contains a plasticizer.

17. The device for delivering the useful agent to an environment of use according to claim 1, wherein the swellable, insoluble polymer is lightly cross-linked.

* * * * *